(12) United States Patent
Kushner

(10) Patent No.: US 8,376,742 B2
(45) Date of Patent: Feb. 19, 2013

(54) DENTAL TRAY

(76) Inventor: Philip Victor Kushner, Miller Place, NY (US)

( * ) Notice: Subject to any disclaimer, the term of this patent is extended or adjusted under 35 U.S.C. 154(b) by 168 days.

(21) Appl. No.: 12/502,348

(22) Filed: Jul. 14, 2009

(65) Prior Publication Data

US 2010/0009313 A1    Jan. 14, 2010

Related U.S. Application Data

(60) Provisional application No. 61/080,368, filed on Jul. 14, 2008.

(51) Int. Cl.
*A61C 9/00* (2006.01)

(52) U.S. Cl. .......................................... 433/37

(58) Field of Classification Search ................ 433/37, 433/93, 140, 94, 136, 138
See application file for complete search history.

(56) References Cited

U.S. PATENT DOCUMENTS 5,516,286 A * 5/1996 Kushner .......................... 433/93
6,241,521 B1 * 6/2001 Garrison ....................... 433/140

* cited by examiner

*Primary Examiner* — Sunil K Singh
(74) *Attorney, Agent, or Firm* — Ivan Posey, Esq.; Kindred I Posey Law Offices

(57) ABSTRACT

A dental tray and system is disclosed. The dental tray may include a frame, an arch bridging two halves of the frame, and a bite block projecting upward from the arch to contact a palate. The system may further include a suction system connected to the frame for suctioning liquid away from an area being worked on. The dental tray may be integral or split in two halves.

17 Claims, 1 Drawing Sheet

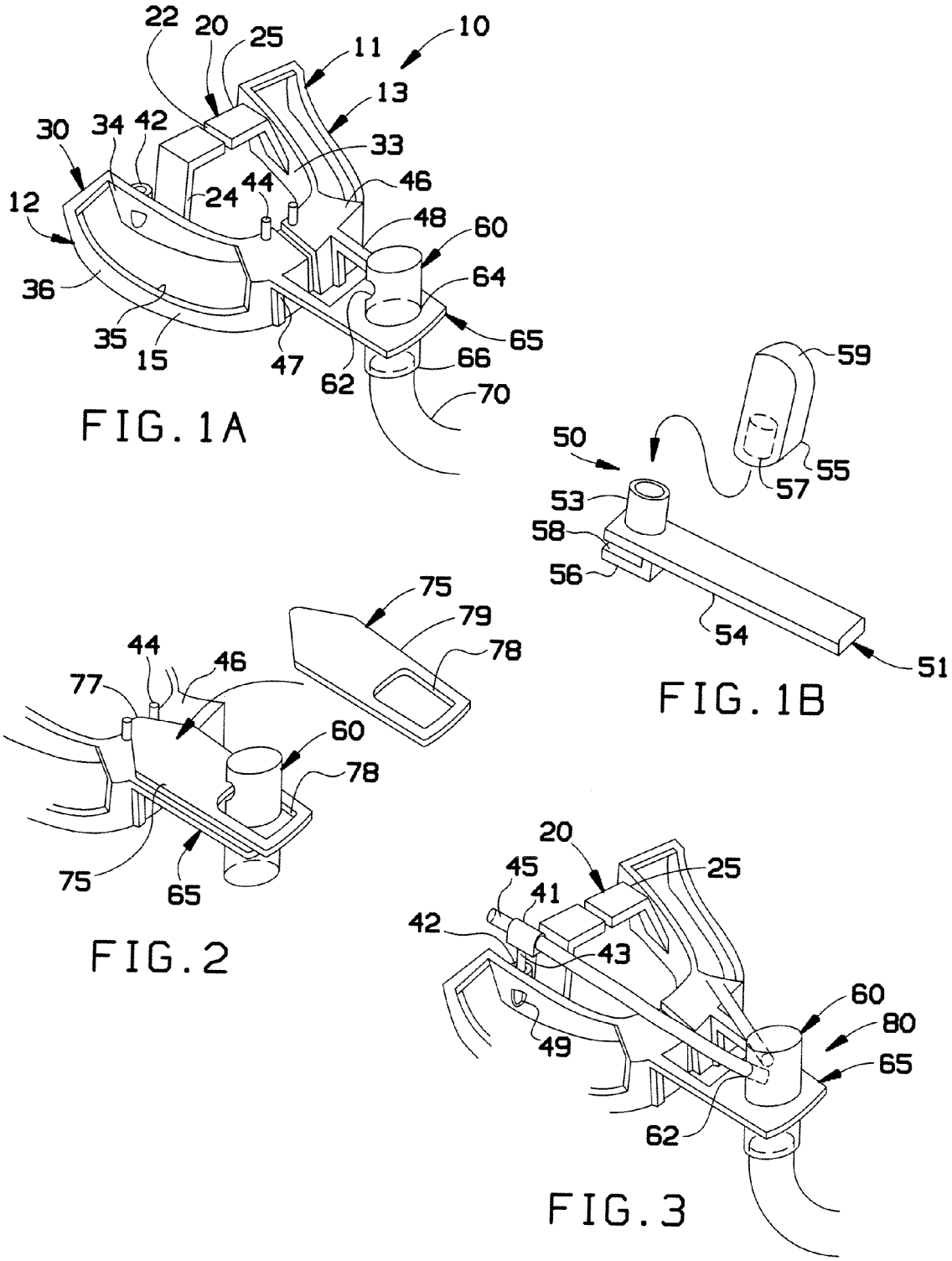

DENTAL TRAY

RELATED APPLICATIONS

This application claims the benefit of priority and incorporates by reference herein, U.S. Provisional application No. 61/080,368, filed Jul. 14, 2008.

BACKGROUND OF THE INVENTION

The present invention generally relates to dental instruments, and more particularly, to a dental tray.

Dentists and other oral professionals occasionally need to maintain a patient's mouth ajar while working on teeth. Some dental work involves maintaining certain areas of teeth dry during a procedure. This can be particularly difficult because the natural tendencies of a mouth are to maintain the mouth moist by introduction of saliva all around the rear of the mouth and the teeth. Another concern for dentists may be maintaining control over the spastic movements of a tongue.

One exemplary procedure that can benefit from controlling moisture and a tongue is the application of sealant along a quadrant of teeth such as molars and bicuspids. The application of sealant to these teeth may be compromised when liquid makes contact with an etched tooth surface and the sealant ineffectively bonds. Applying a sealant to a quadrant of teeth may consume a tediously long session involving numerous breaks to vacuum liquid adjacent to the area or liquid that has entered the working area for application of the sealant. Once the etchant is applied, the quadrant must remain scrupulously dry during application and curing of the sealant. The curing time can be especially onerous for younger patients who may have less control over their tongues and can ruin the process by washing their tongues over the quadrant where sealant has been applied.

Another issue that may arise is maintaining a dental instrument securely in place while performing a procedure. Some prior art devices may move around or partially unseat if the bite-block position does not apply equal seating force to all areas of the tray during, for example, the application of sealants thus allowing liquid to enter areas of the mouth where environmental control is desired. Other known devices may not assist in maintaining a patient's mouth ajar which may fatigue a patient's jaw and cause the patient to temporarily close the mouth and potentially ruin a procedure.

As can be seen, there is a need for a dental tray that supports a jaw and maintains an area of the mouth free from contamination.

SUMMARY OF THE INVENTION

In one aspect of the present invention, a dental tray, comprises a tray frame including a pair of isolation walls defining an opening that surrounds and maintains exposed an area of teeth; an arch connected between the pair of isolation walls; and a bite block attached to the arch, wherein the bite block projects upward from the arch, and wherein the bite block includes an indexed surface indexed to contact a palate.

In another aspect of the present invention, a dental tray system for keeping teeth dry during application of a sealant, comprises a dental tray frame including two split halves, wherein each respective split half includes an opening partially exposing the teeth permitting the application of the sealant; a split arch connected between the two split halves, wherein the arch projects upward from the tray frame; and a bite block unit including a handle and a foam bite block projecting upward from the handle, wherein the bite block unit is attachable to the arch.

These and other features, aspects and advantages of the present invention will become better understood with reference to the following drawings, description and claims.

BRIEF DESCRIPTION OF THE DRAWINGS

FIG. 1A is a perspective view of a dental tray according to an exemplary embodiment of the present invention;

FIG. 1B is a perspective view of a bite block unit for use with the dental tray of FIG. 1A according to an exemplary embodiment of the present invention;

FIG. 2 is a perspective detailed view of an expansion slider for use with the dental tray of FIG. 1A according to another exemplary embodiment of the present invention; and FIG. 3 is a perspective view of a dental tray system incorporating a suction system according to another exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a dental tray system with an arch and a bite block forming a support structure to maintain a mouth ajar and in place while teeth are maintained dry. One exemplary procedure that may benefit from exemplary embodiments of the present invention is the application of sealant to teeth. Exemplary embodiments of the dental tray may provide a tray frame with open areas allowing access to teeth while a suction system removes liquid from the area. A tray frame in the dental tray system may be adjustable to account for mouths of varying size.

Referring now to FIGS. 1A and 1B, a dental tray system 10 may include in general a dental tray 11 and a bite block unit 50. For sake of illustration, the dental tray 11 and bite block unit 50 are depicted as two separate elements, however, it will be understood that in other exemplary embodiments, the bite block unit 50 may be integral to the dental tray 11.

Referring specifically to FIG. 1A, an exemplary embodiment of the dental tray 11 may generally include a tray frame 15 depicted as comprising left and right sides of identical mirrored elements divided by a split 22 traversing between two halves 12 and 13 of the dental tray 11. For sake of illustration, it will be understood that elements are numbered on a single side of the split but may include an analogous element on the other side of the tray frame 15 forming a pair of the element where applicable. The tray frame 15 may include isolation walls 30, an arch 20, and a tray holder 65.

The isolation walls 30 may include an internal wall 34 and an outer wall 36 framing an open area 35 defining where the isolation walls 30 may surround teeth (not shown). The isolation walls 30 may further include an inner surface 33 providing a support surface for the arch 20.

The arch 20 may include top surfaces 25 and arch supports 24. The arch supports 24 may be connected to respective inner surfaces 33 and project upward away from the tray frame 15 and toward a palate (not shown) and at a slight angle from the inner surfaces 33. The top surfaces 25 may be substantially flat and may project away from the arch supports 24 on the same plane as one another.

Referring to FIG. 1B, the bite block unit 50 may generally include a bite block 55 and a handle 51. The bite block 55 may be made from a soft flexible material, such as foam, and may include an indexed tip 59 and a receptacle 57. The handle 51 may include an arm 54, a bracket 56, and a boss 53. The boss 53 and bracket 56 may be on a distal end of the arm 54. The boss 53 may fit into the receptacle 57 supporting the receipt of the bite block 55 so that the bite block 55 projects upward from arm 54 toward a palate (not shown). The bracket 56 and arm 54 may define a slot 58 between each other that may be keyed for receipt over the arch 20.

Thus, in one exemplary operation of the dental tray system 10, the dental tray 11 may be placed around a set of teeth (not shown) so that the isolation walls 30 surround and maintain expose a quadrant of teeth. The arch 20 may fit over a tongue (not shown). The bite block unit 50 may be inserted onto the top surfaces 25 of the arch 20 by fitting the top surfaces 25 into the slot 58 of the bite block unit 50. Thus, when assembled in a patient's mouth (not shown), the isolation walls 30 surround the teeth while the tongue is held in place via the arch 20. Additionally, as may be appreciated, the bite block 55 projects upward from the arch 20 and contacts the palate (not shown) at the indexed tip 59 providing a counterforce downward upon the arch 20 which may provide a relatively uniform pressure downward onto the tray frame 15 around the teeth mitigating lateral movement and tilting of the dental tray 11.

Referring back to FIG. 1A, the tray frame 15 may additionally include hollow support blocks 46 including respectively a post 44 and bridge arms 48 connecting the support blocks 46 to the tray holder 65. The bridge arms 48 may be supported to the support blocks 46 by arched reinforcements 47. The two halves 12 and 13 may thus, be bridged together by the holder 65.

Referring not to FIGS. 1A, 2 and 3, exemplary embodiments of the dental tray system my also include an expansion slider 75 and a suction system 80.

Referring specifically to FIGS. 1A and 3, the suction system 80 may include a vacuum hose 70 connected to a vacuum (not shown) on one end and to a cylinder 60 through an entrance 66 on the other end. The cylinder 60 may be connected to the holder 65 through a hole 64 and the cylinder 60 may include holes 62 receiving straws 45. The straws 45 extend diverging outward from the cylinder 60 toward the rear of the dental tray 11 where liquid may pool up while a patient is lying down. The straws 45 may be supported at a distal portion near the rear of the dental tray 11 and outside of the arch 20 by collars 41 holding the straws 45 up by means of support posts 43. The support posts 43 may be removably inserted into receptacles 42 and fittedly held by pockets 49. Thus, in operation, the straws 45 may be incorporated into the dental tray system 10 when a user is ready to dry the area during an application of sealant. Saliva pooling up near the rear of the mouth may be suctioned away from the open areas 35 through the straws 45 and into the cylinder 60 and out through the vacuum hose 70. The straws 45 may be held steady by virtue of the palate pressing the dental tray 11 down around the teeth. The straws 45 may be protected from the tongue by virtue of the arch 20 surrounding the tongue and the straws 45 being outside of the arch 20.

In embodiments including the split 22, the expansion slider 75 may be incorporated to provide an adjustable dental tray 11 for mouths of varying width. Referring specifically to FIGS. 1A and 2, the expansion slider 75 may include a slot 78 that may fit around the cylinder 60. The expansion slider 75 may include an essentially flat body 79 and a wedged nose 77 opposite the slot 78. In operation, the expansion slider 75 may be set onto the holder 65 with the wedged nose 77 placed on the support blocks 46 between the posts 44. If the dental tray 11 needs to be widened, the expansion slider 75 may be slid forward guided by the cylinder 60 traveling through the slot 78. The forward movement of the expansion slider 75 may drive the wedge nose 77 through the posts 44. As the posts 44 travel along the wedge nose, the split 22 may be widened by virtue of respective halves of the dental tray being separated farther apart.

While the foregoing was described primarily in the context of a dental tray split into two halves, it should be understood that other exemplary embodiments may be employed, such as a unitary dental tray that does not incorporate two separate halves.

It should be understood, of course, that the foregoing relates to exemplary embodiments of the invention and that modifications may be made without departing from the spirit and scope of the invention as set forth in the following claims.

I claim:

1. A dental tray, comprising:
   a tray frame having a first half and a second half, each first and second half including a pair of isolation walls defining an opening that surrounds and maintains an exposed an area of teeth;
   each first and second half having an arch connected between the pair of isolation walls; and
   each first and second half having a separate bite block attached to the arch, wherein the bite block is configured to project upward from the arch toward a palate, and wherein the bite block includes an indexed surface indexed to contact the palate.

2. The dental tray of claim 1, wherein the tray frame comprises two halves including a split between the two halves.

3. The dental tray of claim 1, wherein the bite block is separable from the arch.

4. The dental tray of claim 1, wherein the bite block is attached to an arm including a bracket defining a slot between the bracket and the arm and wherein the arch fits into the slot.

5. The dental tray of claim 2, further comprising an expansion slider attached to the tray frame and a pair of posts attached to each respective half of the tray frame, wherein the expansion slider slidably moves forward to adjustably separate the two halves.

6. A dental tray system for keeping teeth dry during application of a sealant, comprising:
   a dental tray frame including two split halves, wherein each respective split half includes an opening partially exposing the teeth permitting the application of the sealant;
   a split arch connected between the two split halves, wherein the arch projects upward from the tray frame; and
   each of the split halves including a separate bite block unit, capable of attaching a handle and a foam bite block projecting upward from the handle, wherein the bite block unit is attachable to the arch.

7. The dental tray system of claim 6 further comprising a suction system including a vacuum hose and a cylinder receiving the vacuum hose, wherein the cylinder is attached to the dental tray frame at a holder bridging the two halves.

8. The dental tray system of claim 7, further comprising a pair of straws extending diverging outward from the cylinder and disposed outside of the arch.

9. The dental tray system of claim 8 wherein the straws are disposed outside of the arch.

10. The dental tray system of claim 7 further comprising an expansion slider attached to the holder and a pair of posts attached to each respective half of the tray frame on the holder, wherein the expansion slider slidably moves forward to adjustably separate the two halves.

11. The dental tray of claim 6 wherein the foam bite block is configured to project toward a palate and indexed for contact to the palate.

12. The dental tray of claim 1, wherein the bite block is disposed between the isolation walls and over the opening.

13. The dental tray of claim 1, wherein the arch projects upward and away from the tray frame.

14. The dental tray of claim 1, wherein, the arch includes first and second arch supports projecting upward and away from respective inner surfaces of the arch and the bite block is disposed on a top surface of the arch.

15. A dental tray, comprising:
- a frame having a first and a second half;
- a pair of outer isolation walls, each one of said outer isolation walls attached to one of said first and second halves of the frame, the outer isolation walls configured to surround on one side of one or more teeth of a user;
- a pair of opposingly disposed inner isolation walls, each one of said inner isolation walls attached to one of said first and second halves of the frame, the inner isolation walls disposed on a second side of the one or more teeth;
- an inner surface on each inner isolation wall, the inner surfaces defining an open area configured to fit the user's tongue;
- an arch bridging the inner surfaces, positioned over the open area and the user's tongue; and
- a bite block attached to each half of the frame and attached to the arch, each bite block disposed over the user's tongue and disposed to project upward from the arch toward the user's palate.

16. The dental tray of claim 15, where in the arch includes separated portions.

17. The dental tray of claim 15, wherein the frame includes first and second halves and wherein the first and second halves are separated from one another.

* * * * *